United States Patent [19]

Rock et al.

[11] Patent Number: 4,673,748

[45] Date of Patent: Jun. 16, 1987

[54] PROCESS FOR PREPARING 2-OXAZOLINES UTILIZING STANNOUS SALTS OF CARBOXYLIC ACIDS

[75] Inventors: Kenneth Rock, Halesowen; Geoffrey Smith, Quarry Bank, both of England

[73] Assignee: Robinson Brothers Limited, West Midlands, England

[21] Appl. No.: 728,892

[22] Filed: Apr. 30, 1985

[30] Foreign Application Priority Data

May 10, 1984 [GB] United Kingdom ................. 8411928

[51] Int. Cl.$^4$ ............................................ C07D 263/08
[52] U.S. Cl. ..................................... 548/237; 548/239
[58] Field of Search ................................ 548/237, 239

[56] References Cited

U.S. PATENT DOCUMENTS

| | | | |
|---|---|---|---|
| 3,636,157 | 1/1972 | Bozik et al. | 568/433 |
| 3,681,329 | 8/1972 | Litt et al. | 548/239 |
| 4,203,900 | 5/1980 | Kaiser | 548/239 |
| 4,353,029 | 10/1982 | Kaiser et al. | 548/239 |

OTHER PUBLICATIONS

Cagniant et al, Chem. Abst. 90-87187w.
Anderson, Chem. Abst. 102-61957p.
Peterson et al, Chem. Abst. 85-108774z.
Yandovskii et al, Chem. Abst. 79-105116b.
Merck and Co., Inc., Chem. Abst. 99-38364d.
Frump, *Chemical Reviews*, 71, No. 5, 483-505, (1971).

*Primary Examiner*—Donald G. Daus
*Assistant Examiner*—Cecilia Shen
*Attorney, Agent, or Firm*—Linda E. Hall; Stuart R. Suter; Alan D. Lourie

[57] ABSTRACT

This invention relates to a process for preparing 2-oxazolines which comprises cyclodehydrating a hydroxyalkylamide in the presence of a stannous salt of a carboxylic acid. The 2-oxazolines have a variety of uses such as pharmaceutical intermediates, pharmaceuticals and as stabilizers for resins.

8 Claims, No Drawings

PROCESS FOR PREPARING 2-OXAZOLINES UTILIZING STANNOUS SALTS OF CARBOXYLIC ACIDS

This invention relates to a process for the preparation of 2-oxazolines. These oxazolines have a variety of utilities, such as pharmaceutical intermediates, pharmaceuticals and as stablisers for resins; see for example the review by J. A. Frump, Chemical Reviews, Vol. 71, No 5, p 483 (1971).

2-Oxazolines of the formula (I):

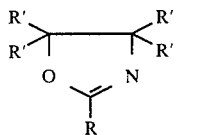
(I)

where R and each R' are hydrogen or an organic group can be prepared by the cyclodehydration of the corresponding hydroxyamides of structure $RCONHCR'_2CR'_2OH$ in the presence of a catalyst. The use of a wide variety of catalysts for this process has been proposed in the literature, and such catalysts include salts of tungsten, molybdenum, manganese, cobalt and rare earth metals (U.S. Pat. No. 3,681,329), ferrous and ferric salts (U.S. Pat. No. 4,203,900), and organic zinc salts (U.S. Pat. No. 4,354,029). These patents refer to the need to use catalysts having a solubility in the hydroxyamides of more than 100 ppm.

It has now been found that carboxylic acid salts of divalent tin are soluble in such hydroxyamides at ambient temperature and are useful catalysts in this cyclodehydration process, in particular the use of these catalysts in the process of the present invention gives ease of handling, a significant aspect in chemical process technology. In addition generally good yields of product are obtained.

The present invention provides a process for preparing an oxazoline of the formula (II):

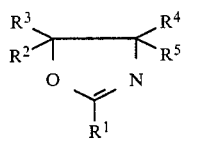
(II)

where $R^1$ is hydrogen or an alkyl, aralkyl or aryl group and $R^2$, $R^3$, $R^4$ and $R^5$ are independently hydrogen or an alkyl group having from 1 to 4 carbon atoms by cyclodehydrating a hydroxyamide of the formula:

in the presence of a metal salt of a carboxylic acid as catalyst, in which the salt is a stannous salt.

The catalyst can be a stannous salt of an aliphatic or aromatic carboxylic acid, for instance an alkylcarboxylic acid having from 1 to 20 carbon atoms such as the acetate, propionate, stearate or oxalate or an aromatic carboxylic acid, such as the benzoate. The salt of a mixture of acids can be used. Preferably the salt is a stannous alkylcarboxylate whose alkyl group has from 5 to 19, especially 5 to 9, carbon atoms, for example a stannous heptoate, octoate, or nonoate, especially stannous n-octoate. The stannous salt is preferably one, that like the n-octoate, is liquid at ambient temperature, is miscible with the starting materials in all proportions, and remains in solution throughout the process.

Suitably $R^1$ is hydrogen, $C_{1-6}$alkyl, phenyl($C_{1-6}$)alkyl for example benzyl or phenyl. More suitably $R^1$ is hydrogen or $C_{1-6}$alkyl.

Preferably in the hydroxyamide groups $R^2$, $R^3$, $R^4$, $R^5$ are all hydrogen and preferably the hydroxyamide is N-(2-hydroxyethyl)-acetamide or N-(2-hydroxyethyl)-propionamide, in which $R^1$ is respectively methyl and ethyl. The hydroxyamides can be prepared by methods described in the literature, for instance U.S. Pat. No. 4,203,900.

Any catalytic amount of the stannous salt can be used: a suitable amount of catalyst is from 0.1 to 5.0% by weight of the hydroxyamide employed, and preferably from 1.0 to 2.0% is used. Particularly suitable temperatures for carrying out the reaction are those within the range of from 200° C. to 250° C.

In operating the process it is convenient to dissolve the catalyst in the hydroxyamide at ambient temperature and to heat the mixture to reaction temperature. The water produced in the reaction can be removed as it is formed, preferably under a reduced pressure of 100 to 350 mm of mercury (14 to 47 kPa) (absolute pressure within apparatus); either water can be removed through a fractionation column arranged to return starting material and product to the reactor under reflux: or water and product can be removed and starting material returned. Preferably the reaction is operated as a continuous process in which the mixture of hydroxyamide and catalyst is continuously supplied to the reactor and the product either collected in the vapour phase with the water, condensed and subsequently separated from it, while the volume of catalyst and by-products in the reactor is maintained constant by continuously drawing off a small proportion of the reactor contents; or only the water is removed in the vapour phase, and product containing small amounts of starting material, by-products and catalyst is continuously drawn off from the reactor to maintain its contents at operational level.

When stannous n-octoate is used as catalyst, the residues containing it are readily removed from the reactor at the end of the process.

The invention is illustrated by the following Examples, in which temperatures are in °C.

EXAMPLES 1 TO 4

N-(2-Hydroxyethyl)-acetamide (100 parts by weight) containing various amounts of stannous n-octoate in solution was heated to 220° in a reaction vessel maintained at a pressure of 150 mm Hg (20 kPa) and fitted with a fractionation column arranged to distil off water and oxazoline product and allow the return of starting material by reflux. Further hydroxyamide (900 parts by weight) was added to the reactor continuously during a period of about 4 hours and when distillation was complete the colourless product was analysed by gas-liquid chromatography to determine the 2-methyl-2-oxazoline content. The amounts of catalyst employed and the yields were as follows.

| Example | Catalyst (parts by weight) | Period of Further addition | Yield of oxazoline (parts by weight) |
|---|---|---|---|
| 1 | 1 | 4¼ hours | 586 (71%) |
| 2 | 5 | 3¼ hours | 710 (86%) |
| 3 | 10 | 3¼ hours | 728 (88.3%) |

-continued

| Example | Catalyst (parts by weight) | Period of Further addition | Yield of oxazoline (parts by weight) |
|---|---|---|---|
| 4 | 50 | 3¼ hours | 694 (84%) |

EXAMPLES 5 TO 7

Processes were carried out as in Examples 2 to 4 except that the starting material was N-(2-hydroxyethyl)propionamide. The amounts of catalysts employed and the yields of 2-ethyl-2-oxazoline were as follows.

| Example | Catalyst (parts by weight) | Period of Further addition | Yield of oxazoline (parts by weight) |
|---|---|---|---|
| 5 | 5 | 3½ hours | 686 (81%) |
| 6 | 10 | 3½ hours | 710 (84%) |
| 7 | 50 | 3½ hours | 694 (82%) |

EXAMPLE 8

To N-(2-hydroxyethyl)-propionamide (100 parts by weight) was added stannous n-octoate (1 part) and the resulting mixture was heated to and maintained at 200°–230° under reduced pressure (150 mm Hg, 20 kPa) in a reactor fitted with a fractionating column for removal of water and product and retention of starting material by reflux. A mixture of water and 2-ethyl-2-oxazoline began to distil off at a reactor temperature of 195°. A mixture of the starting material (900 parts) and catalyst (9 parts) was then continuously added to the reactor at a rate equal to the rate of formation of the distillate, the total heating period being 6 hours.

Analysis by gas-liquid chromatography of the water-white distillate obtained showed that it contained 2-ethyl-2-oxazoline (736 parts, 87%), which could be isolated in a pure state (b.p. 128°–9°/760 mm Hg or 100 kPa) by standard methods.

EXAMPLE 9

N-(2-Hydroxyethyl)formamide (100 parts by weight) containing stannous n-octoate (5 parts by weight) in solution was heated to 220° C. in a reaction vessel maintained at a pressure of 250 mm Hg (33 kPa) and fitted with a fractionation column arranged to distil off water and oxazoline product and allow the return of starting material by reflux. Further formamide (140 parts by weight) was added to the reactor continuously during a period of about 4 hours to give a distillate product containing 2-oxazoline (yield 43%).

EXAMPLE 10

N-(2-Hydroxyethyl)benzamide (200 parts by weight) and stannous octoate (1 part by weight) were charged to the standard reaction vessel as one lot. The mixture was heated to 230° C. at 250 mm Hg (33 kPa) and maintained at these conditions for 4 hours by when water had ceased to distil over. The residues were distilled under vacuum to give 2-phenyl-2-oxazoline (yield 58%), b.p. 115° C./1 mm Hg (0.13 kPa).

EXAMPLE 11

In an analogous manner to that of Example 10, N-(2-hydroxyethyl)phenylacetamide (200 parts by weight) and stannous octoate (1 part by weight) gave 2-benzyl-2-oxazoline (yield 50%), b.p. 120° C./1 mm Hg (0.13 kPa).

EXAMPLE 12

To N-(2-hydroxyethyl)-propionamide (100 parts by weight) was added stannous n-octoate (1 part) and the resulting mixture was heated to and maintained at about 220° under reduced pressure (300 mm Hg, 40 kPa) in a reactor fitted with a fractionating column for removal of water and product and retention of starting material by reflux. A mixture of water and 2-ethyl-2-oxazoline began to distil off at a reactor temperature of 195°. A mixture of the starting material (1200 parts) and catalyst (12 parts) was then continuously added to the reactor at a rate equal to the rate of formation of the distillate, the total heating period being 8 hours.

Analysis by gas-liquid chromatography of the water-white distillate obtained showed that it contained 2-ethyl-2-oxazoline (1062 parts, 96.5%), which could be isolated in a pure state (b.p. 128°–9°/760 mm Hg or 100 kPa) by standard methods.

EXAMPLES 13 TO 17

N-(2-Hydroxyethyl)propionamide (200 parts by weight) was mixed with the catalyst under test and part of the mixture (24 parts by weight) was heated at 220° C. in a reaction vessel maintained at 250 mm Hg (33 kPa). The vessel was fitted with a fractionation column arranged to distil off water and the oxazoline product and to allow the return of the starting material by reflux. The remainder of the mixture was added continuously to the vessel during a period of about 4 hour, and when distillation was complete, the colourless product was analysed by gas-liquid chromatography to determine the 2-ethyl-2-oxazoline content.

The amounts and nature of catalyst employed and yields were as follows:

| Catalyst | Parts by Weight | period of continuous addition | yield of 2-ethyl-2-oxazoline (Parts by weight) |
|---|---|---|---|
| stannous octoate | 2 | 3½ hour | 146.9 (86.8%) |
| stannous octoate | 1 | 3½ hour | 147.9 (87.4%) |
| stannous acetate | 1 | 3¾ hour | 144.8 (85.6%) |
| stannous stearate | 1 | 3½ hour | 148.8 (87.9%) |
| stannous oxalate | 1 | 3½ hour | 148.1 (87.5%) |
| for comparison no catalyst | | 8 hour | 116.2 (68.7%) |

EXAMPLE 18

N-(2-Hydroxypropyl)propionamide (200 parts by weight) and stannous octoate (1 part by weight) were heated in a similar manner to Examples 13–17. After 4 hours of continuous addition the distillate was treated with solid potassium hydroxide, the organic layer was azeotroped with cyclohexane and the residue was distilled at 135° C./749 mm Hg (98 kPa) to give 2-ethyl-5-methyl oxazoline (yield 85.3%).

What is claimed is:

1. A process for preparing an oxazoline of the formula (II):

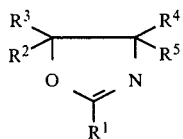 (II)

where $R^1$ is hydrogen, an alkyl, or a phenyl ($C_{1-6}$) alkyl group and $R^2$, $R^3$, $R^4$ and $R^5$ are independently hydrogen or an alkyl group having from 1 to 4 carbon atoms by cyclodehydrating a hydroxyamide of the formula:

$$R^1CONHCR^2R^3CR^4R^5OH$$

in the presence of a metal salt of a carboxylic acid as catalyst, in which the salt is a stannous salt.

2. A process according to claim 1, in which the stannous salt is a stannous alkylcarboxylate whose alkyl group has from 5 to 19 carbon atoms.

3. A process according to claim 2, in which the alkyl group has from 5 to 9 carbon atoms.

4. A process according to claim 3, in which the salt is stannous n-octoate.

5. A process according to any one of claims 1 to 4, in which $R^1$ is hydrogen or $C_{1-6}$alkyl.

6. A process according to any one of claims 1 to 4, in which the hydroxyamide is N-(2-hydroxyethyl)-acetamide or N-(2-hydroxyethyl)-propionamide.

7. A process according to claim 5, in which the hydroxyamide is N-(2-hydroxyethyl)-acetamide or N-(2-hydroxyethyl)-propionamide.

8. A process according to claim 1, wherein the catalyst is in liquid form.

* * * * *